United States Patent [19]

Bohls

[11] Patent Number: 4,553,532
[45] Date of Patent: Nov. 19, 1985

[54] EXTERNALLY VALVED SHUNT FOR CARDIOPULMONARY BYPASS PUMP

[75] Inventor: Fred O. Bohls, Austin, Tex.

[73] Assignee: Thomas M. Runge, Austin, Tex.

[21] Appl. No.: 514,601

[22] Filed: Jul. 18, 1983

[51] Int. Cl.⁴ .......................... A61M 1/03; A61F 1/24
[52] U.S. Cl. ...................................... 128/1 D; 623/3; 417/412; 417/478
[58] Field of Search ............................ 128/1 D; 3/1.7; 417/412, 478

[56] References Cited

U.S. PATENT DOCUMENTS 3,518,033  6/1970  Anderson .......................... 3/1.7 X
4,143,425  3/1979  Runge ................................. 3/1.7

Primary Examiner—Ronald L. Frinks
Attorney, Agent, or Firm—B. P. Fishburne, Jr.

[57] ABSTRACT

To decrease hemolysis and reduce the cost of single use disposable tubing used during surgery, valve elements pivotally suspended in the bypass pump compression chamber respond to gravity and variations in fluid pressure within the shunt and act entirely on the exterior of the shunt to cyclically control blood flow therethrough. Interior valves for the shunt tubing are entirely eliminated.

7 Claims, 6 Drawing Figures

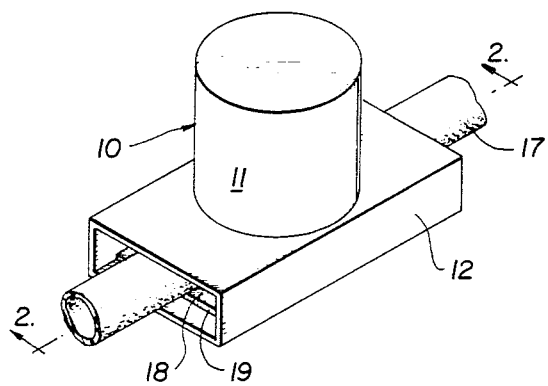
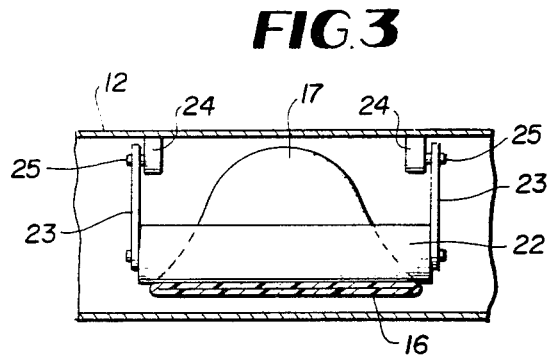
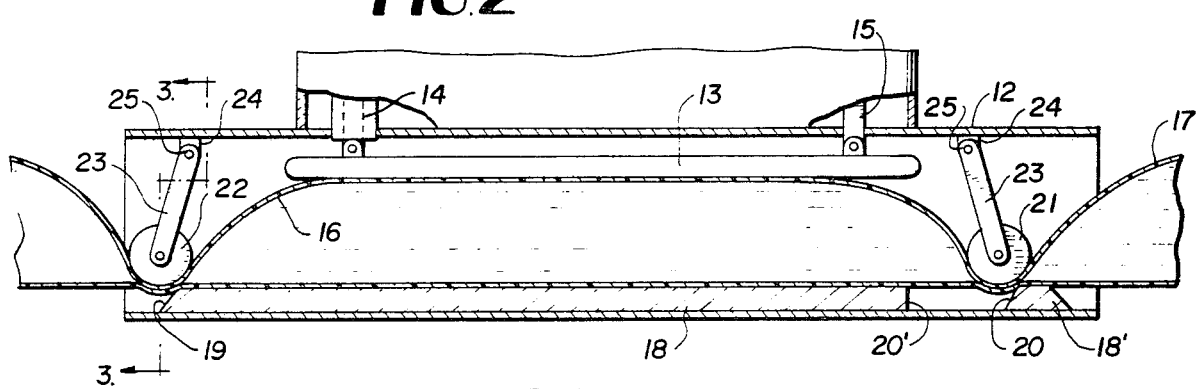
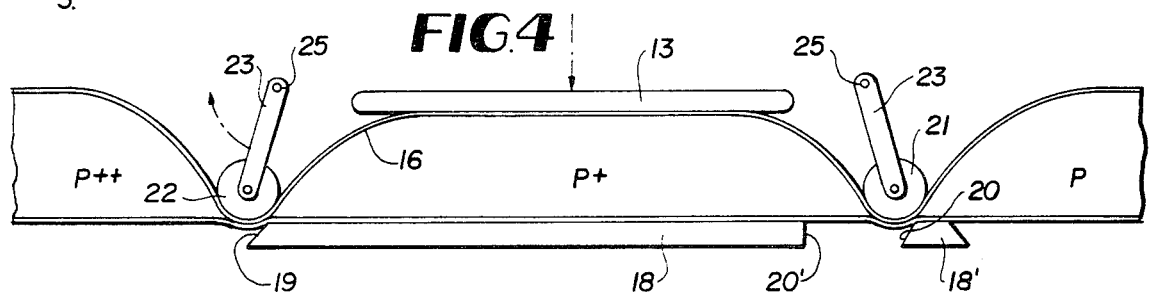
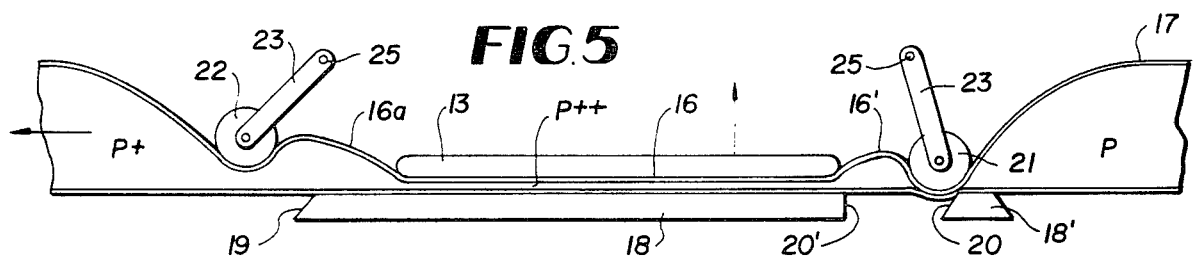
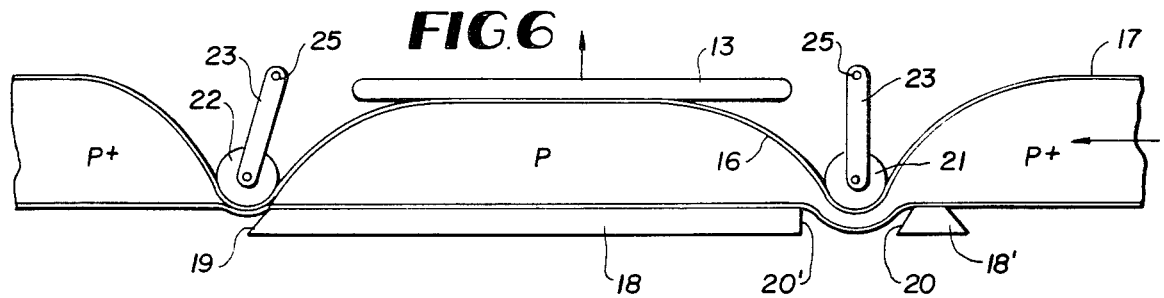

EXTERNALLY VALVED SHUNT FOR CARDIOPULMONARY BYPASS PUMP

BACKGROUND OF THE INVENTION

The present invention seeks to improve on the type of cardiopulmonary bypass pumping apparatus shown in prior U.S. Pat. Nos. 4,134,425 and 4,293,961, both issued to Runge. In both of these patents, a compressible tubing shunt is utilized in the compression chamber of a pulsatile flow pump. The compressible shunt in both patents is equipped with interior proximal and distal valves near opposite ends of the pump compression chamber. The manufacturing of shunt tubing from polyurethane or the like with internal valving is quite expensive, particularly where such tubing is used for one operation only and then discarded. Also, the internal shunt valving causes some hemolysis.

Because of the above, it is highly desirable to provide a cardiopulmonary bypass pumping system in which valveless tubing for the shunt may be employed, and it is the objective of the present invention to satisfy this requirement in an efficient, economical and operationally safe and reliable manner.

More particularly, in accordance with the present invention a pair of gravity biased freely pivotally suspended valve roller elements are provided within the compression chamber or housing of the pump near opposite ends of the chamber to act on the exterior of the shunt tubing so as to close off and open the shunt tubing to control blood flow therethrough in a prescribed repetitive cycle of operation. The gravity biased valve elements respond directly to fluid pressure in the shunt at two points near opposite ends of the pump compression plate beneath which a compressible sack of the shunt is located.

Other objects and advantages of the invention will become apparent during the course of the following description.

BRIEF DESCRIPTION OF THE DRAWINGS

FIG. 1 is a perspective view of a valveless shunt and cardiopulmonary bypass pump according to the present invention.

FIG. 2 is an enlarged vertical section through the shunt and pump taken on line 2—2 of FIG. 1.

FIG. 3 is a transverse vertical section taken on line 3—3 of FIG. 2.

FIGS. 4, 5 and 6 are partly schematic views depicting the operation of external shunt valves during an operating cycle.

DETAILED DESCRIPTION

Referring to the drawings in detail wherein like numerals designate like parts, a cardiopulmonary bypass pump 10 substantially in accordance with the aforementioned patents includes a drive mechanism housing 11 fixed to an open ended compression chamber or housing 12 which may be rectangular in cross section. Within this housing, a flat pump compression plate 13 carried by drive members 14 and 15 of the pump mechanism is moved in reciprocation on a generally vertical path to cyclically compress and release a sack portion 16 of a tubing shunt 17 which extends through the open ended housing 12. The tubing shunt 17 can be formed of polyurethane or similar synthetic material. The tubing shunt contains no internal valves. It is used with the pump mechanism for one surgical operation and is then discarded, as previously explained.

Fixed to the bottom wall of the housing 12 is a flat valve plate 18 having a beveled edge 19 at its downstream or systemic end. The valve plate 18 is cut off vertically at 20' near its upstream or reserve end, and a small plate segment 18' having a beveled edge 20 is fixed to the bottom wall of housing 12 in spaced relationship to the cut off edge 20'. The two beveled edges 19 and 20 are steeply inclined as shown.

Within the compression housing 12 near its ends and on opposite sides of the compression plate 13 is a pair of transverse axis preferably cylindrical gravity biased valve elements 21 and 22. These roller-like valve elements are located adjacent to the beveled edges 19 and 20' of valve plate 18. They are located between the two side walls of the open ended housing 12.

The valve elements 21 and 22 are suspended on arms 23 from overhead lugs 24 fixed to the top wall of housing 12 through suitable pivot elements 25. In this manner, the gravity biased valve elements are free-hanging within the housing 12. In addition to being influenced by gravity, the valve elements 21 and 22 are acted upon by fluid (blood) pressure within the tubing shunt 17, as will be fully explained in the description of the operating cycle. The valve elements 21 and 22 in cooperation with the valve plate 18 form two independently operating external pinch valves for the flexible tubular shunt 17 on opposite sides of its compressible sack portion 16.

OPERATION

Beginning with FIG. 4, the pump compression plate 13 is just beginning to exert downward pressure on the filled compressible sack 16. Both external valves are closed due to the engagement of the valve elements 21 and 22 with beveled edges 19 and 20. The tubing shunt 17 is therefore pinched closed at two points by the valves. The upstream valve 21-20 on the reserve side of the shunt is closed due to the angle of the adjacent lever or arm 23 and the increasing pressure in the sack 16, which is greater than the upstream reserve side pressure in the shunt 17. Thus the element 21 is engaged with the beveled edge 20 to act as a pinch valve in its closed position at this time. The downstream or systemic valve 22-19 is closed in FIG. 4 because systemic pressure in the shunt is greater than the pressure in the sack 16, and this greater pressure acting with gravity holds the element 22 against the beveled edge 19. It is to be noted that gravity assists in closing the pinched valve consisting of element 22 and beveled edge 19, whereas gravity assists in opening the upstream pinched valve comprised of element 21 and beveled edge 20. There is no blood flow into or out of the sack 16 under the conditions shown in FIG. 4. The upstream or reserve and sack pressures are equal until the plate 13 begins to exert downward pressure on the sack 16. With this arrangement, pinch valve 21-20 is certain to close when the compression plate 13 starts its downward travel, FIG. 4.

Progressing to FIG. 5, the compression plate 13 has compressed the sack 16 and the sack is emptying. Upstream valve 20-21 remains closed due to the angle of arm 23 and the effect of increased pressure created in a bulge 16' as a result of the compression plate 13 moving down. The pressure in the bulge 16' at this time is greater than the upstream reserve pressure in the shunt 17. The downstream valve 22-19, FIG. 5, is open because the pressure in bulge 16a caused by compression of sack 16 is greater than downstream systemic pressure in the shunt, the pivoted gravity biased valve element 22 responding to fluid pressure and rising to permit an outflow of blood from the compressed sack.

Referring to FIG. 6, the sack 16 fills passively as pump compression plate 13 rises. The upstream external valve 21-20 opens due to gravity and also due to upstream reserve pressure being greater than sack pressure at this time. Downstream valve 22-19 closes because systemic pressure is now greater than pressure within the sack 16. Gravity also assists in closing downstream valve 22-19.

The operating cycle is completed by progressing from the arrangement in FIG. 6 back to the condition shown in FIG. 4.

It is to be understood that the form of the invention herewith shown and described is to be taken as a preferred example of the same, and that various changes in the shape, size and arrangement of parts may be resorted to, without departing from the spirit of the invention or scope of the subjoined claims.

I claim:

1. A cardiopulmonary bypass pumping apparatus comprising a valveless compressible shunt adapted to convey blood, a pump having a compression chamber through which the compressible shunt extends and a compression plate operatively mounted in the compression chamber at one side of the shunt, a pair of guided movable biased pinch valve elements within the compression chamber near its opposite ends and on opposite sides of the compression plate and responding to variations in fluid pressure within a sack portion of the shunt between the valve elements which is compressed cyclically by the compression plate to open and close independently in a sequence to deliver blood in a required manner through the shunt, a cooperative valve plate on the bottom wall of said compression chamber having spaced abutment surfaces engageable with the guided movable biased pinch valve elements, and said pinch valve elements being gravity biased whereby one valve element tends to engage one abutment surface and the other valve element tends to disengage the other abutment surface.

2. A cariopulmonary bypass pumping apparatus as defined in claim 1, and the gravity biased pinch valve elements being carried by swingable extension arms which are pivotally attached to the compression chamber.

3. A cardiopulmonary bypass pumping apparatus comprising a valveless compressible shunt adapted to convey blood, a pump having a compression chamber through which the compressible shunt extends and a compression plate operatively mounted in the compression chamber at one side of the shunt, a pair of guided movable biased pinch valve elements within the compression chamber near its opposite ends and on opposite sides of the compression plate and responding to variations in fluid pressure within a sack portion of the shunt between the valve elements which is compressed cyclically by the compression plate to open and close independently in a sequence to deliver blood in a required manner through the shunt, a cooperative valve plate on the bottom wall of said compression chamber having spaced abutment surfaces engageable with the guided movable biased pinch valve elements, said spaced abutment surfaces comprising substantially parallel inclined surfaces whose top corners are displaced relative to the lower corners toward the upstream side of the apparatus, and said pinch valve elements being biased by gravity so that one such valve element tends to move toward the downstream abutment surface and the other valve element tends to move away from the upstream abutment surface.

4. A cardiopulmonary bypass pumping apparatus comprising a valveless compressible shunt adapted to convey blood, a pump having a compression chamber through which the compressible shunt extends and a compression plate operatively mounted in the compression chamber at one side of the shunt, a pair of guided movable biased pinch valve elements within the compression chamber near its opposite ends and on opposite sides of the compression plate and responding to variations in fluid pressure within a sack portion of the shunt between the valve elements which is compressed cyclically by the compression plate to open and close independently in a sequence to deliver blood in a required manner through the shunt, the compression chamber being defined by an open-ended housing having a through passage for the shunt, a valve plate fixed on the bottom wall of said housing and having a substantially flat compression face disposed opposite to the compression plate and having spaced abutment surfaces near its opposite ends adapted to engage the biased pinch valve elements, the biased pinch valve elements comprising weighted elements, and pivoted swingable suspension arms attached to and carrying said weighted elements and being pivotally connected with said housing.

5. In a cardiopulmonary bypass pump adapted to operate with a valveless compressible tubing shunt, a pump compression passage means through which the shunt extends and including a valve plate external to the shunt on one side of the shunt, a pump compression plate movable across the passage means toward and away from the valve plate and being disposed externally to the other side of the shunt to cyclically compress and release a sack portion of the shunt within the passage means in cooperation with the valve plate, and a pair of spaced movable valve elements external to the shunt within the passage means and being adapted to compressively engage the shunt across the shunt, one valve element being biased by gravity to engage and pinch the shunt closed against an abutment surface of the valve plate, and the other valve element being biased by gravity away from pinching engagement with the shunt against another abutment surface of the valve plate spaced from the first mentioned abutment surface.

6. In a cardiopulmonary bypass pump as defined in claim 5, and the gravity biased external valve elements comprising cylindrical elements whose axes are parallel and across the longitudinal axis of the shunt, and pivoted suspension arms carrying the valve elements and being pivotally attached to the pump compression passage means.

7. A cardiopulmonary bypass pumping apparatus comprising a valveless compressible bypass shunt adapted to convey blood, a pump having a shunt compression chamber through which the compressible shunt extends, said compression chamber having a wall and said wall having a pair of spaced abutment surfaces, a compression plate operably mounted in said compression chamber on the side of the shunt away from said wall and adapted cyclically to compress a sack portion of the shunt in the region between said spaced abutment surfaces against said wall to expel blood from the sack portion, and a pair of suspended swingable gravity biased valve elements on the compression chamber and being external to the shunt and being adapted cyclically to pinch the shunt closed against said abutment surfaces, one valve element being biased by gravity toward engagement with one abutment surface and the other valve element being biased by gravity away from engagement with the other abutment surface, and both valve elements being adapted to be moved by portions of the shunt having pressurized blood therein toward and away from said abutment surfaces.

* * * * *